United States Patent [19]

Schaffer et al.

[11] Patent Number: 4,917,861

[45] Date of Patent: Apr. 17, 1990

[54] PALLADIUM ALLOY CONTAINING GERMANIUM AND/OR LITHIUM AND DENTAL RESTORATIONS UTILIZING SAME

[75] Inventors: Stephen P. Schaffer, Hamburg; Patrick J. McCabe, Tonawanda, both of N.Y.

[73] Assignee: Pierce & Stevens Corporation, Buffalo, N.Y.

[21] Appl. No.: 271,578

[22] Filed: Nov. 15, 1988

[51] Int. Cl.⁴ .............................................. C22C 5/04
[52] U.S. Cl. ..................................... 420/463; 420/464
[58] Field of Search ........................ 420/463, 464, 465; 428/450; 433/207

[56] References Cited

U.S. PATENT DOCUMENTS

| | | | |
|---|---|---|---|
| 4,201,577 | 5/1980 | Ingersoll et al. | 420/580 |
| 4,336,290 | 6/1982 | Tsai | 420/463 |
| 4,387,072 | 6/1983 | Schaffer | 420/463 |
| 4,399,096 | 8/1983 | Agarwal et al. | 420/463 |
| 4,518,564 | 5/1985 | Prasad | 420/464 |
| 4,608,229 | 8/1986 | Lanam et al. | 420/464 |
| 4,717,539 | 1/1988 | Morisey | 420/489 |

FOREIGN PATENT DOCUMENTS

| | | | |
|---|---|---|---|
| 3304183 | 4/1984 | Fed. Rep. of Germany | 420/464 |
| 0107438 | 6/1983 | Japan | 420/465 |
| 0186437 | 8/1986 | Japan | 420/464 |

Primary Examiner—L. Dewayne Rutledge
Assistant Examiner—David W. Schumaker
Attorney, Agent, or Firm—Waldron & Associates

[57] ABSTRACT

Dental restorations are made of a palladium alloy which consists essentially of, on a weight basis, 50–85 percent palladium; 5–40 percent of at least one metal selected from the group consisting of copper and cobalt; 1–15 percent gallium; up to 5 percent of a modifier selected from the group consisting of nickel, gold, indium, ruthenium, tin and mixtures thereof; from 0.005 up to 1 percent, ordinarily less than about 0.2 percent, of an oxygen scavenging component which is a member selected from the group consisting of germanium, lithium, and mixtures thereof; and up to 0.5 percent of a grain refiner selected from the group consisting of rhenium and iridium. The alloy is free of boron.

7 Claims, No Drawings

PALLADIUM ALLOY CONTAINING GERMANIUM AND/OR LITHIUM AND DENTAL RESTORATIONS UTILIZING SAME

BACKGROUND OF THE INVENTION

1. Field of the Invention

This invention relates to the field of noble metal alloys and to their use in the manufacture of dental restorations.

2. The Prior Art

As is well known, dental casting alloys should provide a high degree of biocompatibility or inertness to the conditions in the mouth and good physical properties so that they will provide long lived usage. In addition, those alloys which are used to provide castings upon which porcelain coatings may be applied must provide good bonding characteristics to the porcelain coatings and other characteristics which are compatible with the porcelain coatings, such as similar coefficient of thermal expansion, avoidance of discoloration of the porcelain, etc. Lastly, the alloy should process well during casting and be useful with commercially available porcelains.

Previously, gold alloys, usually gold/platinum alloys, were preferred as dental casting materials because they have provided a highly desirable balance of properties. The commercially available dental porcelains have been formulated so as to be compatible therewith.

Over the years, much effort has gone into developing alloys for dental applications with higher strength and lower cost (more readily available) metals. For example, cobalt base alloys almost completely displaced gold alloys in the area of partial dentures in the mid 1930s. And, more recently, nickel base alloys have made a significant impression in porcelain substrates alloys (the subject of this application).

Within the noble metals area, much effort has been expended to use the nobility, strength and lower cost of palladium as the base for new alloy systems. Also in the 1930s, high palladium and palladium based alloys were attempted, but the need to deoxidize palladium was not recognized. The problems with high palladium alloys was believed, until recently, to be hydrogen dissolved in therein.

A number of gold/palladium and palladium/silver alloys have been developed which provide a high degree of compatibility with porcelain and satisfactory physical and mechanical properties. However, silver has a tendency to migrate at the porcelain firing temperature and to discolor the porcelain. This silver migration and its discoloration of porcelain make porcelain selection and porcelain firing control critical in order to produce aesthetic porcelain fused to alloy restorations, particularly for anterior use.

While reduction or elimination of silver content minimized the discoloration effect, it made control of the alloy's thermal expansion (contraction) more difficult. Elimination of gold has had the same effect on thermal expansion characteristics. Nevertheless, silver and gold are elements which are very useful in formulating alloys with the desirable coefficient of thermal expansion for compatibility with porcelain, about $13.8-15 \times 10^{-6}$in/in/°C. In one of co-applicant's prior applications, Ser. No. 174,749 filed Aug. 4, 1980, now U.S. Pat. No. 4,350,526, there is disclosed a palladium alloy which has overcome the discoloration problem.

However, even the palladium alloys of co-applicant's patent require close control in the porcelain firing step and selection of the porcelains used in connection therewith. The generally available dental porcelains were formulated for use with high gold content alloys so as to exhibit a coefficient of thermal expansion which is typically 5-10 percent lower than the high gold content alloys. This results in placing the porcelain coating in compression after cooling from the firing temperature, thereby producing a stronger restoration when it is subjected to tensile loading.

The reduction or elimination of the gold content in some of the substitute alloys has caused difficulty in maintaining a sufficiently high thermal coefficient of expansion, which is desirably in the range of $13.8-15 \times 10^{-6}$in/in/°C. As indicated in co-applicant's above identified patent, silver has been used to replace gold in an effort to provide a suitable coefficient of thermal expansion but it tends to migrate at the porcelain firing temperatures, and to cause a distinct uncontrolled discoloration of the porcelain which is aesthetically unacceptable.

Alloys for use as ceramo-metal restorations must also exhibit a desired balance of physical and mechanical properties. To properly support the fragile porcelain layer or the restoration, the alloy must have a yield strength at 0.1 percent offset of over 40,000 psi. In addition, the alloy needs high temperature strength to withstand the forces applied to the restoration while the porcelain is being fired in place.

While standard tensile tests are possible at porcelain firing temperatures, 950–1000° C., a more reliable test of strength for the special circumstances of porcelain fired to metal dental restorations is the "sag" test. This test is performed on a strip of alloy $1 \times 10$ mm in cross section and 50+ mm long. The strip is supported on knife edge supports 50 mm apart and a static load applied. The assembly is placed in a standard dental porcelain firing furnace and heated in the same manner as a normal dental restoration. The amount of deflection is measured and this "sag" is an indication of the high temperature strength of the alloy. Sag in the 5 mm range is unacceptable. Sag of from 1–5 mm requires special precautions be made to prevent the sag. The desired value is less than 1 mm.

Moreover, a dental casting alloy must be able to be soldered before the porcelain firing cycle. Since porcelain is fired at approximately 1000° C., the alloy must possess a solidus above about 1100° C. to allow the solder to flow without starting to melt the casting. However, in order to allow the alloy to be cast with standard equipment found in dental laboratories, the liquidus temperature must not be greater than 1400° C. Lastly, the alloy must also exhibit good bonding to dental porcelains.

Many palladium based and high palladium content alloys may meet the physical and mechanical requirements noted but are completely unusable due to a certain characteristic of palladium. Palladium has a high affinity for oxygen, and much of the early failure to develop high palladium alloys was the failure to recognize this problem.

The alloys of U.S. Pat. No. 4,387,072 of one of the instant co-applicants, met many of the criteria noted above and provided boron as a deoxidizer. That alloy does, however, have a rather high and undesirable degree of sag at firing temperatures, as will be detailed in the examples. This high sag is indicative of low strength at the firing temperature of the porcelain.

The primary object of the present invention is to provide an alloy with sufficient high temperature strength such that porcelain may be fired thereon without causing the restoration to deform through sag.

It is another object of the present invention to provide a novel palladium dental alloy which exhibits a highly desirable balance of casting properties and physical properties, together with biocompatibility and freedom from discoloration of porcelain coatings which are fired thereon and which provide good bonding of the porcelain coatings fired thereon.

It is also an object to provide such an alloy which is relatively inexpensive when compared to gold and platinum alloys and which provides a balance of properties which is superior thereto.

Still another object is to provide such an alloy which may be cast and soldered relatively easily and which will provide excellent bonding to porcelain coatings fired thereon and avoid discoloration thereof.

A further object is to provide dental restorations comprising castings of such alloys and porcelain coatings fired thereon, and wherein the porcelain coatings are essentially free from any discoloration and exhibit a high degree of bonding strength to the casting.

A very particular object of the present invention is to provide an alloy which is an improvement on that defined in U.S. Pat. No. 4,387,072.

SUMMARY OF THE INVENTION

It has now been found that the foregoing and related objects may be readily attained in a palladium alloy which consists essentially of, on a weight basis, 50–85 percent palladium; 5–40 percent of at least one metal selected from the group consisting of copper and cobalt; 1–15 percent gallium; up to 5 percent of a modifier selected from the group consisting of nickel, gold, indium, ruthenium, tin and mixtures thereof; from 0.005 up to 1 percent, ordinarily less than about 0.2 percent, of an oxygen scavenging component which is a member selected from the group consisting of germanium, lithium, and mixtures thereof; up to 0.5 percent of a grain refiner selected from the group consisting of rhenium and iridium and mixtures thereof. The alloy is free of boron.

Preferably, the alloys have from 0.01 up to 0.1 percent of an oxygen scavenging component which is a member selected from the group consisting of germanium, lithium, and mixtures thereof and utilize gold as the modifier in an amount of 1–3 percent by weight. Copper is preferred over cobalt because of cost, and the copper and/or cobalt is desirably used in an amount of 5–15 percent. The palladium content is desirably in the range of 70–82 percent by weight of the alloy. Rhenium and/or iridium is provided as a grain modifier in about 0.05–0.2 percent.

A highly advantageous alloy is one containing 76–80 percent palladium, 9–12 percent copper and/or cobalt, 8–11 percent gallium, the oxygen scavenging component will be about 0.01 percent lithium and about 0.05 percent germanium, 1–3 percent of the modifier which is preferably gold, and 0.05–0.2 percent rhenium.

The dental restorations comprise a casting of the aforementioned alloy and a porcelain coating fired upon a portion of the casting. The porcelain coatings are substantially free from discoloration and are firmly bonded to the casting.

DETAILED DESCRIPTION OF THE PREFERRED EMBODIMENTS

As hereinbefore indicated the alloys of the present invention use palladium as the principal component, and use copper and/or cobalt, and gallium as the other essential components. They desirably contain a small amount of the oxygen scavenging component and a small amount of selected modifying elements. In addition, they may contain as grain refining components, rhenium and/or iridium.

The alloys must contain at least 50 percent palladium and may contain as much as 85 percent palladium. Preferably, the alloy contains 70–82 percent palladium in order to obtain the desired nobility and an optimum balance of properties.

The copper and/or cobalt content may vary from 5–40 percent by weight of the total composition and is preferably in the range of 5–15 percent by weight. This component reduces the melting point of the alloy while minimizing the tendency to form additional microstructural phases.

To provide both strength to the alloy and the necessary oxide formation to effect bonding with the porcelain coating, gallium must be used in an amount of 1–15 percent and preferably in the range of 3–12 percent. Amounts above 15 percent will tend to adversely affect other properties.

From 0.005 up to 1 percent, generally less than about 0.2 percent, of an oxygen scavenging element, which is a member selected from the group consisting of germanium, lithium, and mixtures thereof is desirably added and preferably in the range of 0.01–0.1 percent to serve as a scavenger for oxygen and oxides either present in the alloy or formed during the casting process.

It has been found that the oxygen scavenging component of the present invention is fully effective at much lower proportions than those required when oxygen scavenging effects are provided by boron. Both the reduction in the proportions of the component and the nature of the specific elements employed appear to contribute to the improved properties of the finished alloys made with the present invention. When the amount of the oxygen scavenging component, whether germanium, lithium, or a mixture of both, is employed in excess of about 0.2 percent of the alloy, an embrittling effect is encountered. It is generally not preferred to add the component in amounts greater than required to afford the necessary degree of oxygen scavenging.

The group of modifier metals comprised of nickel, gold, indium, ruthenium, tin and mixtures thereof is utilized in the range of up to 5 percent to aid in the prevention of discoloration of the porcelain during firing while having some minor benefits on the desired coefficient of thermal expansion. Amounts of as little as 0.3 percent have been found to provide significant benefits. Generally, amounts in excess of 3.0 percent provide no additional benefit, and amounts in excess of 5 percent adversely affect the balance of properties of the alloy and should not be employed. Preferably, gold is used in amounts of 1–3 percent.

For most applications, it is desirable to incorporate rhenium and/or iridium in an amount of up to 0.5 percent by weight in order to effect grain refinement. When such a grain refining component is included, it is preferably present in the range of 0.05–0.15 percent. However, desirable casting and other properties have been obtained without the incorporation of a grain refining component.

The alloys produced in accordance with the present invention routinely exhibit a solidus temperature in excess of 1100° C. in order to withstand porcelain firing temperatures of about 1000° C., while the liquidus temperature of the alloy is well below 1400° C. to permit facile processing in the equipment generally available in dental laboratories. To provide a good compatible alloy for use with present commercial porcelains, the alloy has a coefficient of thermal expansion within the range of $13.8-15 \times 10^{-6}$ in/in/°C. (600-20° C.). The yield strength of the alloy at 0.1 percent offset is in excess of 50,000 psi. The sag is below 1 mm. Moreover, the alloys of the present invention have both high corrosion resistance and tarnish resistance and do not discolor the porcelain.

Illustrative of the efficacy of the alloys of the present invention are the following examples, wherein all parts are parts by weight unless otherwise indicated.

EXAMPLE ONE

An alloy was prepared containing 78.84 percent palladium, 10.0 percent copper, 9.0 percent gallium, 2.0 percent gold, 0.05 percent germanium, 0.01 percent lithium, and 0.10 percent iridium.

Specimens cast therefrom were found to exhibit a liquidus of 1210° C., a solidus of 1180° C., a Vickers hardness of 310 and to have a yield strength at 0.1 percent offset of 92,000 psi. Its tensile elongation was 20%, coefficient of thermal contraction (expansion) was $14.5 \times 10^{-6}$ in/in/°C. over the temperature range of 600-20° C. The measured sag was 0.4 mm.

Several commercial porcelains available from different manufacturers were fired against castings of this alloy in accordance with the manufacturers' specifications. In all instances, the bond strength was excellent and the fired restorations found to be free from any discoloration of the porcelain. Exposure to corrosion testing of the cast sample indicated freedom from tarnish. No evidence of sag in three-unit bridges was found. No porcelain-metal separation or delamination was found.

EXAMPLE TWO

To test the high temperature strength (sag) effect of various potential deoxidizers, including boron of U.S. Pat. No. 4,387,072, sag tests were run on nine variants of the basic formula; changing only the oxygen scavenger component(s). The palladium used, in all cases, was high purity (99.9+%) with low oxygen content. The problems associated with oxygen and oxides were thus circumscribed. The test results are shown in Table I below.

TABLE I

|    | I | II | III | IV | V | VI | VII | VIII | IX |
|----|---|----|----|----|---|----|----|------|----|
| Pd | 78.65 | 78.65 | 78.65 | 78.65 | 78.60 | 78.65 | 78.90 | 77.97 | 78.89 |
| Cu | 10.00 | 10.00 | 10.00 | 10.00 | 10.00 | 10.00 | 10.00 | 10.42 | 10.00 |
| Ga | 9.00 | 9.00 | 9.00 | 9.00 | 9.00 | 9.00 | 9.00 | 9.38 | 9.00 |
| Au | 2.00 | 2.00 | 2.00 | 2.00 | 2.00 | 2.00 | 2.00 | 2.08 | 2.00 |
| B  | 0.20 | 0.20 | 0.20 | 0.20 | 0.20 | 0.20 |     |      |      |
| Ir | 0.10 | 0.10 | 0.10 | 0.10 | 0.10 | 0.10 | 0.10 | 0.10 | 0.10 |
| Ta | 0.05 |     |     |     |     |     |     |      |      |
| W  |     | 0.05 |    |     |     |     |     |      |      |
| V  |     |     | 0.05 |   |     |     |     |      |      |
| Zr |     |     |    | 0.05 |    |     |     |      |      |
| Ge |     |     |    |     | 0.10 | 0.05 |    | 0.05 |      |
| Li |     |     |    |     |     |     |     |      | 0.01 |
| Sag | 5.13 | 3.98 | 3.46 | 3.38 | 6.26 | 1.69 | 0.56 | 0.73 | 0.61 |

TABLE I-continued

|    | I | II | III | IV | V | VI | VII | VIII | IX |
|----|---|----|----|----|---|----|----|------|----|
| (mm) | | | | | | | | | |

The sag for all alloys containing boron was more than 1 mm. For alloys, including the sample in Example one, that contained no boron, the sag was less than 1 mm. Alloy VII, with no deoxidizer also had a low sag value (0.56 mm) and confirms that boron is the cause of the high sag. A limited amount of germanium (0.05%) improves the sag caused by boron, 1.69 mm for alloy VI, but higher germanium (0.1%) seemingly added to the sag caused by boron, 6.26 mm for alloy V.

EXAMPLE THREE

To compare the value of the oxygen scavenging component of the present invention with a boron component and with the omission of any oxygen scavenging component, three alloys were made and evaluated:

A first alloy of 80.5 percent palladium, 10.0 percent copper, 9.0 percent gallium, and 0.5 percent boron was prepared, and test specimens cast therefrom. A second alloy formulation containing the same amount of palladium, copper and gallium, but no boron, was prepared and test specimens cast therefrom. A third alloy formulation containing the same amount of palladium, copper and gallium, but no boron, and 0.05 percent germanium and 0.01 percent lithium, was prepared and test specimens cast therefrom. The test results of these three alloys are presented in Table II below.

TABLE II

|  | First Alloy Prior Art Alloy With B | Second Alloy Prior Art Alloy W/O B | Third Alloy Alloy of this Invention |
|---|---|---|---|
| Melting Range (°F.) | 2040-2020 | 1960-2200 | 2160-2205 |
| Vickers Hardness (Porcelain Cycle) | 360 | 350 | 310 |
| Yield Strength (1% offset-psi) | 130,500 | 80,600 | 92,000 |
| Elongation (%) | 18.8 | 9.1 | 20.0 |
| Coefficient of Thermal Expansion (600-20° C.) | $14.5 \times 10^{-6}$ | $14.2 \times 10^{-6}$ | $14.5 \times 10^{-6}$ |
| Weight Sag (mm) | 1.32 | 0.56 | 0.40 |

Thus, it can be seen from the foregoing detailed specification and examples that the alloys of the present invention provide a highly desirable balance of properties for use with dental porcelains including good casting characteristics, good physical properties, high tarnish resistance, solderability, and substantial elimination of any tendency for discoloration of porcelain coatings fired thereon. The alloys may be processed readily using available dental laboratory equipment and may be used with currently available commercial porcelains. The result is highly attractive, useful and long lived dental restorations. The disadvantages apparently caused by the boron content in the prior art alloy, i.e. low strength at firing temperatures, is entirely overcome.

I claim:

1. A dental alloy having exceptional high temperature strength consisting essentially of:
   a. 50-85 percent by weight palladium;
   b. 5-40 percent by weight of at least one metal selected from the group of cobalt and copper;

c. 1-15 percent by weight gallium;
d. up to 5 percent by weight of a modifier selected from the group consisting of nickel, gold, indium, ruthenium, tin and mixtures thereof;
e. from about 0.01 up to about 0.05 percent by weight of an oxygen scavenging component which is a member selected from the group consisting of germanium, lithium, and mixtures thereof; and
f. up to 0.5 percent by weight of a grain refiner selected from the group consisting of rhenium, iridium, and mixtures thereof, said alloy having an exceptional high temperature strength characterized by a sag test value of less than 1 mm at a firing temperature of 950-1000° C., and further having a coefficient of thermal expansion of about $13.8-15 \times 10^{-6}$in/in/°C., a solidus temperature of at least 1100° C., a liquidus temperature of not more than 1400° C., Vickers hardness greater than 150, offset yield strength at 0.1 percent offset of greater than 40,000 p.s.i., and tensile elongation greater than 6 percent.

2. The dental alloy of claim 1 wherein the palladium content is 70-82 percent, the cobalt and/or copper content is 5-15 percent, the gallium content is 3-12 percent, and the modifier content is 1-3 percent.

3. The dental alloy of claim 2 wherein the modifying element is gold.

4. The dental alloy of claim 2 wherein the palladium content is 76-80 percent, the cobalt and/or copper content is provided by copper in the amount of 9-12 percent, the gallium content is 8-11 percent, the modifying element is provided by gold in the amount of 1-3 percent; and the grain refiner comprises 0.05-0.15 percent thereof.

5. A dental restoration comprising:
a. a casting of a dental alloy consisting essentially of
(i) 50-85 percent by weight palladium;
(ii) 5-40 percent by weight of at least one metal selected from the group of cobalt and copper;
(iii) 1-15 percent by weight gallium;
(iv) up to 5 percent by weight of a modifier selected from the group consisting of nickel, gold, indium, ruthenium, tin and mixtures thereof,
(v) from about 0.01 up to about 0.05 percent by weight of an oxygen scavenging component which is a member selected from the group consisting of germanium, lithium, and mixtures thereof, and
(vi) up to 0.5 percent by weight of a grain refiner selected from the group consisting of rhenium, iridium, and mixtures thereof, said alloy having an exceptional high temperature strength characterized by a sag test value of less than 1 mm at a firing temperature of 950-1000° C., and further having a coefficient of thermal expansion of about $13.8-15 \times 10^{-6}$in/in/°C., a solidus temperature of at least 1100° C., a liquidus temperature of not more than 1400° C., Vickers hardness greater than 150, offset yield strength at 0.1 percent offset of greater than 40,000 p.s.i., and tensile elongation greater than 6 percent; and
b. a porcelain coating upon a portion of said casting, said coating being firmly bonded to said casting and being substantially free from discoloration.

6. The dental restoration of claim 5 wherein said alloy contains 70-82 percent by weight palladium, 5-15 percent by weight cobalt and/or copper, 3-12 percent by weight gallium, 1-3 percent by weight of the modifier, and 0.05-0.15 percent by weight of the grain refiner.

7. The dental restoration of claim 6 wherein the modifying element is gold.

* * * * *